United States Patent
Trieu et al.

(10) Patent No.: US 9,724,149 B2
(45) Date of Patent: Aug. 8, 2017

(54) SURGICAL IMPLANT SYSTEM AND METHOD

(71) Applicant: Warsaw Orthopedic, Inc., Warsaw, IN (US)

(72) Inventors: Hai H. Trieu, Cordova, TN (US); Brian Burd, Olive Branch, MS (US); Amanda McMahon, Collierville, TN (US); Michael Simmons, Moscow, TN (US)

(73) Assignee: Warsaw Orhtopedic, Inc., Warsaw, IN (US)

( * ) Notice: Subject to any disclaimer, the term of this patent is extended or adjusted under 35 U.S.C. 154(b) by 994 days.

(21) Appl. No.: 13/789,180

(22) Filed: Mar. 7, 2013

(65) Prior Publication Data

US 2014/0257408 A1    Sep. 11, 2014

(51) Int. Cl.
*A61B 17/58* (2006.01)
*A61B 17/88* (2006.01)
*A61B 17/86* (2006.01)
*A61B 17/68* (2006.01)

(52) U.S. Cl.
CPC .......... *A61B 17/8875* (2013.01); *A61B 17/68* (2013.01); *A61B 17/8615* (2013.01); *A61B 17/8685* (2013.01); *A61B 17/866* (2013.01); *A61B 17/8695* (2013.01); *A61B 17/888* (2013.01)

(58) Field of Classification Search
CPC ... B25B 15/001; B25B 15/004–15/008; B25B 15/02; B25G 1/04; B25G 1/10; F16B 5/0233; F16B 5/0283; A61B 17/888; A61B 17/8883; A61B 17/8886; A61B 17/8888; A61B 17/8891; A61B 17/8894
USPC ....... 81/436, 451, 461, 177.5; 606/300–321; 411/546, 384, 916
See application file for complete search history.

(56) References Cited

U.S. PATENT DOCUMENTS

| | | | |
|---|---|---|---|
| 4,060,115 A * | 11/1977 | Bocanegra Marquina | B25G 1/10 74/557 |
| 4,612,918 A | 9/1986 | Slocum | |
| 4,773,402 A | 9/1988 | Asher et al. | |
| 4,961,740 A | 10/1990 | Ray et al. | |
| 5,026,373 A | 6/1991 | Ray et al. | |
| 5,108,397 A | 4/1992 | White | |
| 5,334,205 A | 8/1994 | Cain | |
| 5,490,851 A | 2/1996 | Nenov et al. | |
| 5,498,265 A * | 3/1996 | Asnis | A61B 17/74 606/315 |
| 5,593,407 A | 1/1997 | Reis | |
| 5,669,909 A | 9/1997 | Zdeblick et al. | |
| 5,713,904 A | 2/1998 | Errico et al. | |

(Continued)

*Primary Examiner* — Todd E Manahan
*Assistant Examiner* — Jessica Weiss (57) ABSTRACT

A surgical instrument includes a first member defining a longitudinal axis and including a drive interface engageable with a first surface of a bone fastener. The first surface is configured for penetrating a sacrum. A second member includes a drive interface engageable with a second surface of the bone fastener to translate the second surface relative to the first surface such that the second surface engages an outer non-articular surface of an ilium to draw separated articular surfaces of the sacrum and the ilium into fixation. In some embodiments, systems and methods are disclosed. Systems and methods are disclosed.

20 Claims, 7 Drawing Sheets

(56) References Cited

U.S. PATENT DOCUMENTS

| | | | |
|---|---|---|---|
| 5,928,239 A | 7/1999 | Mirza | |
| 5,964,768 A | 10/1999 | Huebner | |
| 5,997,541 A * | 12/1999 | Schenk | A61B 17/68 606/104 |
| 6,048,344 A * | 4/2000 | Schenk | A61B 17/68 606/304 |
| 6,053,916 A | 4/2000 | Moore | |
| 6,224,603 B1 | 5/2001 | Marino | |
| 6,299,615 B1 | 10/2001 | Huebner | |
| 6,319,254 B1 * | 11/2001 | Giet | A61B 17/863 606/104 |
| 6,635,059 B2 | 10/2003 | Randall et al. | |
| 6,648,903 B1 | 11/2003 | Pierson, III | |
| 6,948,408 B1 * | 9/2005 | Lee | B25B 15/008 81/436 |
| 7,582,107 B2 * | 9/2009 | Trail | A61B 17/863 606/304 |
| 7,625,395 B2 | 12/2009 | Muckter et al. | |
| 7,637,954 B2 | 12/2009 | Michelson | |
| 7,648,509 B2 | 1/2010 | Stark | |
| 7,670,383 B1 | 3/2010 | Brown et al. | |
| 8,118,849 B2 * | 2/2012 | Wahl | A61B 17/8605 606/305 |
| 8,905,697 B2 * | 12/2014 | Gong | E04D 3/3606 411/371.1 |
| 8,998,968 B1 * | 4/2015 | Brow | A61B 17/8695 606/306 |
| 2002/0198527 A1 | 12/2002 | Muckter | |
| 2006/0106382 A1 | 5/2006 | Gournay et al. | |
| 2006/0161154 A1 | 7/2006 | McAfee | |
| 2006/0161261 A1 | 7/2006 | Brown et al. | |
| 2007/0027543 A1 | 2/2007 | Gimble et al. | |
| 2007/0233125 A1 * | 10/2007 | Wahl | A61B 17/8605 606/250 |
| 2007/0265621 A1 | 11/2007 | Matthis et al. | |
| 2007/0270879 A1 | 11/2007 | Isaza et al. | |
| 2008/0021456 A1 | 1/2008 | Gupta et al. | |
| 2008/0039843 A1 | 2/2008 | Abdou | |
| 2008/0140082 A1 | 6/2008 | Erdem et al. | |
| 2009/0018660 A1 | 1/2009 | Roush | |
| 2009/0024174 A1 | 1/2009 | Stark | |
| 2009/0099610 A1 | 4/2009 | Johnson et al. | |
| 2009/0216238 A1 | 8/2009 | Stark | |
| 2009/0259261 A1 | 10/2009 | Reiley | |
| 2010/0010496 A1 | 1/2010 | Isaza et al. | |
| 2010/0036440 A1 * | 2/2010 | Morris | A61B 17/72 606/320 |
| 2010/0094290 A1 | 4/2010 | Vaidya | |
| 2010/0106200 A1 | 4/2010 | Stark | |
| 2010/0131011 A1 | 5/2010 | Stark | |

\* cited by examiner

SURGICAL IMPLANT SYSTEM AND METHOD

TECHNICAL FIELD

The present disclosure generally relates to medical devices for the treatment of musculoskeletal disorders, and more particularly to a surgical system for delivering and/or fastening implants with a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility. For example, disorders of the sacroiliac (SI) joint can cause low back and radiating buttock and leg pain in patients suffering from degeneration and laxity of the SI joint.

Non-surgical treatments, such as medication, rehabilitation and exercise can be effective, however, may fail to relieve the symptoms associated with these disorders. Surgical treatment of these disorders includes stabilization and/or arthrodesis procedures, which may employ implants such as bone fasteners, connectors and plates, to provide stability to a treated region. Arthrodesis may include fastening such implants with tissue to immobilize a joint. This disclosure describes an improvement over these prior art technologies.

SUMMARY

In one embodiment, a surgical instrument is provided. The surgical instrument includes a first member defining a longitudinal axis and including a drive interface engageable with a first surface of a bone fastener. The first surface is configured for penetrating a sacrum. A second member includes a drive interface engageable with a second surface of the bone fastener to translate the second surface relative to the first surface such that the second surface engages an outer non-articular surface of an ilium to draw separated articular surfaces of the sacrum and the ilium into fixation. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical implant system are discussed in terms of medical devices for the treatment of musculoskeletal disorders and more particularly, in terms of a surgical implant system for delivering and/or fastening implants with a surgical site and a method for treating a spine. In one embodiment, the surgical implant system includes a surgical implant driver and a bone screw. In one embodiment, the surgical implant driver includes a first drive and a second drive. This configuration provides a dual drive feature configured to facilitate translation of an anchoring portion of the bone screw and a compression portion of the bone screw. In some embodiments, the surgical implant system and methods of use disclosed provide stability and maintains structural integrity while reducing stress on an SI joint. In some embodiments, the surgical implant system and methods of use disclosed may be employed to treat musculoskeletal disorders including SI dysfunction or syndrome, dehydration, destabilization and/or laxity.

In one embodiment, the surgical implant system includes a screw having a lag configuration for SI joint fusion with compression capability. The screw comprises a distal thread for engaging sacral bone and a non-threaded proximal section that enables compression. In one embodiment, the screw defines a screw head for compression capability. In some embodiments, the screw head defines a hexalobe drive insert. In one embodiment, the surgical implant system comprises a screw including a fixation surface with serrations or a washer having one or a plurality of spikes. In one embodiment, the washer can include projections and threading. In one embodiment, the washer includes serration patterns on its proximal surface.

In one embodiment, the surgical implant system comprises a cannulated compression screw and method of use to stabilize the SI joint for fusion. In one embodiment, the surgical implant system comprises a method comprising the steps of: under image guidance such as fluoroscopy, inserting a guidewire across the SI joint at a trajectory; drilling and tapping across the SI joint along the guidewire; with the guidewire in place, inserting an anchoring section of the screw through the ilium into the sacrum until appropriate depth is reached; and advancing a reinforcement section of the screw across the SI joint while compressing the SI joint using a compression section. The surface of the screw assembly may be treated such that it would enhance osseointegration (for example, textured, anodized, hydroxyapatite (HA)-coated and/or porous coating). In one embodiment, the screw may be fabricated from one or more materials such as titanium, titanium alloys, cobalt-chrome (CoCr) alloys, stainless steel, polyetheretherketone (PEEK) and/or carbon-reinforced PEEK. In one embodiment, the screw can be implanted without the use of guidewire. In one embodiment, a cannulation channel can be used for injection of biological or pharmacological agents.

In one embodiment, a method is provided, similar to the method described below with regard to FIGS. 1-7, which comprises the steps of making a skin mark and an incision; inserting an elongated pin through soft tissue and ilium into the sacrum under fluoroscopy; placing a cannula, with or without a handle, over the pin to protect soft tissue during subsequent drilling; drilling along the pin through the SI joint and stopping at a selected depth within the sacrum; optional tapping, for example, if the screw thread is not self-tapping; optional preparation of the SI joint for accelerated fusion (for example, decorticate, preparation, clean, cause bleeding); measuring the drill depth of the bony section (for example, 50 millimeters (mm)); selecting a compression screw with a selected range of length (for example, medium screw with 45-55 mm adjustable length); setting initial screw length between 55 and 50 mm and/or at a telescoped length of 55 mm; inserting the compression screw until its distal tip reaches the drill depth; shortening screw length and compressing the SI joint as the screw length reaches about 50 mm; and closing the surgical wound. In one embodiment, the final screw length after compressing the SI joint is expected between 50 and 45 mm. In some embodiments, if the screw is perforated, bone graft can be injected into the prepared joint via injection.

In one embodiment, a method is provided, similar to the method described below with regard to FIGS. 1-7, which comprises the step of pre-drilling a passage through the ilium and sacrum before inserting the screw. In some embodiments, tapping is not required as the distal screw thread can be designed for self-tapping.

In one embodiment, a method is provided, similar to the method described below with regard to FIGS. 1-7, which comprises the step of adjusting screw length prior to insertion and based on a measured depth. In one embodiment, the method can include the step of selecting a drill depth. For example, if the drill depth of the SI bone section is about 50 mm, a compression screw with an adjustable range of 55 to 45 mm can be used, which allows for measurement error and compression. In some embodiments, the telescoping length of the screw can be adjusted after implantation to achieve or enhance compression of the SI joint. For example, the distal threaded portion of the screw is fixed in the sacrum such that shortening the telescoping length after implantation can include shortening the telescoping screw length to push the ilium toward the sacrum to cause the SI joint to narrow resulting in compression effect.

In one embodiment, the surgical implant system comprises surgical navigation technology to guide drilling, tapping and screw insertion. In one embodiment, the compression screw can be cannulated for injecting biologics into the SI joint space. In one embodiment, the surgical implant system comprises a nerve monitor to prevent potential nerve damage while drilling, tapping and screw insertion.

In one embodiment, the surgical implant system comprises a screw that compresses the SI joint such that the gap within the joint is reduced to facilitate bone to bridge across the joint for faster fusion. In some embodiments, the SI joint surfaces are approximated to cause more resistance to their relative motions. In some embodiments, this configuration reduces shear stresses imposed on the screw disposed across the joint, which results in more stable fixation and avoidance of screw fracture. In some embodiments, this configuration avoids shear stress being transferred to the trans-joint screws or implants, and as such fewer and/or smaller screws can be used to stabilize the SI joint.

In some embodiments, one or all of the components of the surgical implant system may be disposable, peel-pack, pre-packed sterile devices. One or all of the components of the surgical implant system may be reusable. The surgical implant system may be configured as a kit with multiple sized and configured components.

In some embodiments, the surgical implant system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical implant system of the present disclosure may be employed with other osteal and bone related applications, including those associated with diagnostics and therapeutics. In some embodiments, the disclosed surgical implant system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical implant system of the present disclosure may also be alternatively employed with procedures for treating the lumbar, cervical, thoracic, sacral and pelvic regions of a spinal column. The surgical implant system of the present disclosure may also be used on animals, bone models and other non-living substrates, such as, for example, in training, testing and demonstration.

The surgical implant system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical implant system including at least one driver and at least one bone fastener, related components and methods of employing the surgical implant system in accordance with the principles of the present disclosure. Alternate embodiments are also disclosed. Reference will now be made in detail to the exemplary embodiments of the present disclosure, which are illustrated in the accompanying figures. Referring to FIGS. 1-5, there is illustrated components of a surgical implant system 10 including a surgical instrument 12 and an orthopedic implant, such as, for example, a bone fastener 14.

The components of surgical implant system 10 can be fabricated from biologically acceptable materials suitable for medical applications, including metals, synthetic polymers, ceramics and bone material and/or their composites, depending on the particular application and/or preference of a medical practitioner. For example, the components of surgical implant system 10, individually or collectively, can be fabricated from materials such as stainless steel alloys, commercially pure titanium, titanium alloys, Grade 5 titanium, super-elastic titanium alloys, CoCr alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including PEEK, polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), HA-TCP, calcium sulfate, or other resorbable polymers such as polyaetide, polyglycolide, polytyrosine carbonate, polycaroplaetohe and their combinations. Various components of surgical implant system 10 may have material composites, including the above materials, to achieve various desired characteristics such as strength, rigidity, elasticity, compliance, biomechanical performance, durability and radiolucency or imaging preference. The components of surgical implant system 10, individually or collectively, may also be fabricated from a heterogeneous material such as a combination of two or more of the above-described materials. The components of surgical implant system 10 may be monolithically formed, integrally connected or include fastening elements and/or instruments, as described herein.

Spinal implant system 10 is employed, for example, with an open or mini-open, minimal access and/or minimally invasive including percutaneous surgical technique to deliver and fasten an implant, such as, for example, bone fastener 14 at a surgical site within a body of a patient, for example, a section of a spine. In one embodiment, system 10 is configured to treat SI joint disorders including those caused by degeneration or trauma. In one embodiment, system 10 is adapted to immobilize opposing naturally separated surfaces of a SI joint. In some embodiments, the components of spinal implant system 10 are configured to fix a spinal rod, connector and/or plate to a spine to treat various spine pathologies, such as those described herein.

Figure 1:
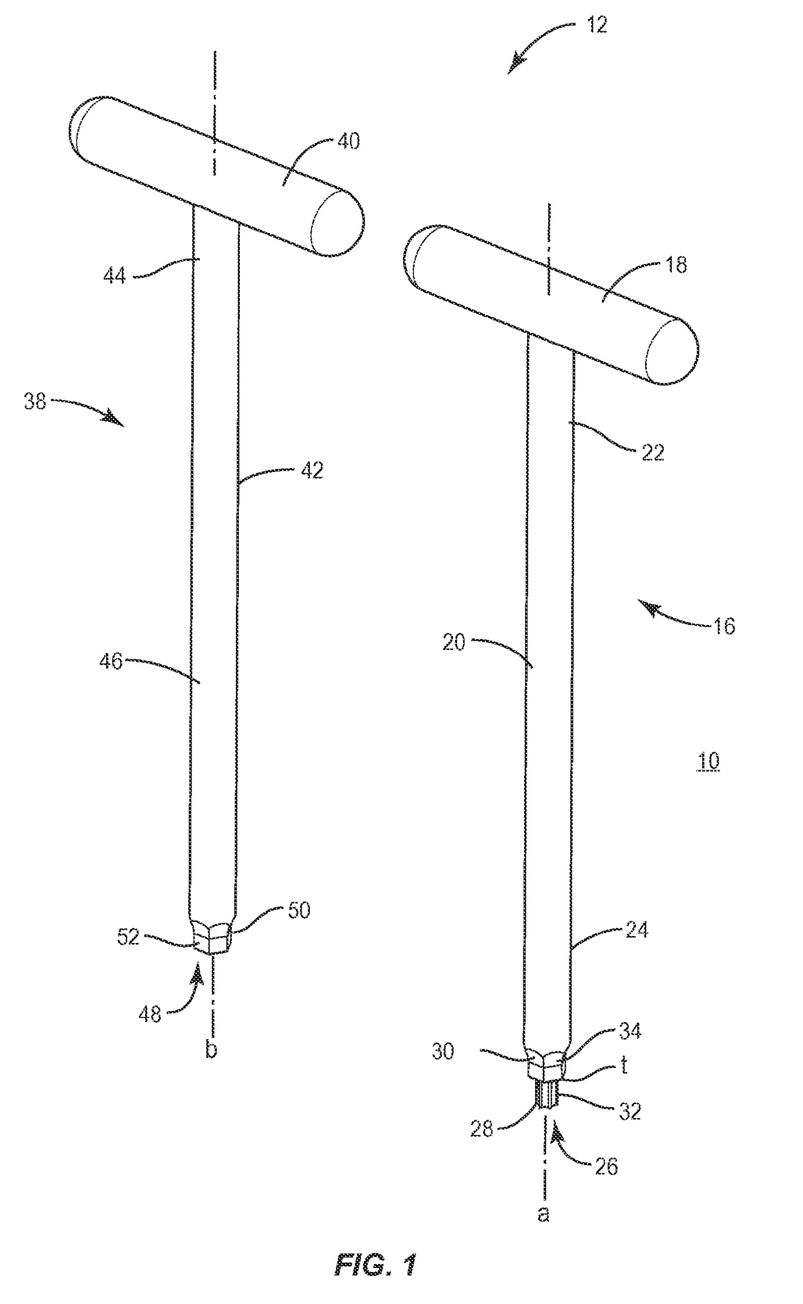
FIG. 1 is a perspective view of components of one embodiment of a surgical implant system in accordance with the principles of the present disclosure.
Figure 2:
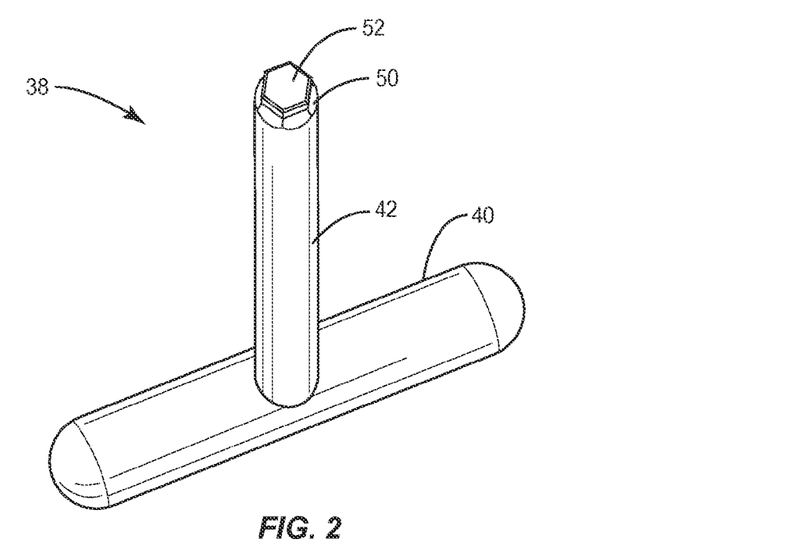
FIG. 2 is a perspective view of a component shown in FIG. 1.

Surgical instrument 12 includes a member, such as, for example, an anchor driver 16. Driver 16 includes a T-handle 18 configured for manipulation by a practitioner and an elongated shaft 20 extending in a linear configuration therefrom. In some embodiments, driver 16 may include alternate handle configurations, such as, for example, coaxial, offset or staggered, or pistol grip. In some embodiments, shaft 20 may extend in alternate orientations, such as, for example, arcuate, undulating, staggered, offset, angular and/or include one or a plurality of shaft members.

Shaft 20 extends between a first end, such as, for example, a proximal end 22 and a second end, such as, for example, a distal end 24 including an engagement portion 26. Shaft 20 has a cylindrical cross sectional configuration. In some embodiments, all or only a portion of shaft 20 may have alternate cross section configurations, such as, for example, oval, oblong, triangular, square, polygonal, irregular, uniform, non-uniform, offset, staggered, tubular and/or tapered. Shaft 20 defines a longitudinal axis a.

Portion 26 includes an outer surface defining a surface 28 and a surface 30 disposed in a serial configuration along axis a, with surface 28 being distal to surface 30. Surface 28 defines a drive interface 32 engageable with a surface of a bone fastener, as described herein. Drive interface 32 has a hexalobular drive and/or bit configuration. Surface 30 defines a drive interface 34 engageable with a surface of a bone fastener, as described herein. Drive interface 34 has a hex drive and/or bit configuration. In some embodiments, interface 32, interface 34 and/or the surfaces of the bone fastener can include variously configured drive and/or socket surfaces, such as, for example, slotted, Phillips, cruciate, pozidriv, square, pin-in-hex-socket, Torx, tri-wing, torq-set, spanner head, triple square, polydrive, one-way, spline drive, double hex, bristol, pentalobular, thread forms, triangular, star, irregular, uniform, non-uniform, offset, staggered, and/or tapered.

Interfaces 32, 34 are separated by a transition line t extending transverse to axis a. Interface 32 has a first diameter and interface 34 has a second diameter that is greater than the first diameter. Portion 26 includes an edge 36 disposed between interfaces 32, 34 and adjacent transition line t. Interfaces 32, 34 and edge 36 are disposed in an orientation such that portion 26 includes a stepped configuration adjacent distal end 24.

Figure 3:
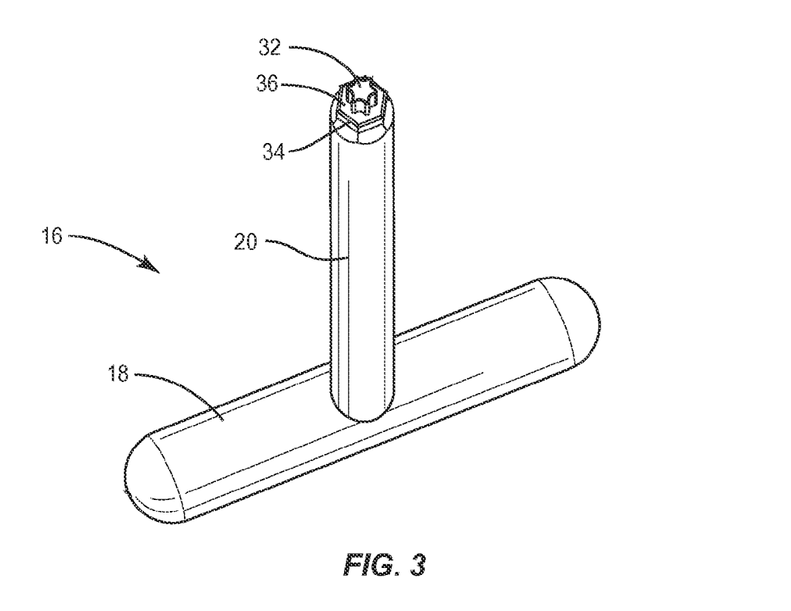
FIG. 3 is a perspective view of a component shown in FIG. 1.

Surgical instrument 12 includes a member, such as, for example, a compression driver 38. Driver 16 is separate from driver 38. In some embodiments, driver 16 may be connected, fastened and/or attached with driver 38.

Driver 38 includes a T-handle 40 configured for manipulation by a practitioner and an elongated shaft 42 extending in a linear configuration therefrom. In some embodiments, driver 38 may include alternate handle configurations, such as, for example, those described herein.

Shaft 42 extends between a first end, such as, for example, a proximal end 44 and a second end, such as, for example, a distal end 46 including an engagement portion 48. Shaft 42 has a cylindrical cross sectional configuration. In some embodiments, all or only a portion of shaft 42 may have alternate cross section configurations, such as, for example, those described herein. Shaft 42 defines a longitudinal axis b.

Portion 48 includes an outer surface defining a surface 50. Surface 50 defines a drive interface 52 engageable with a surface of a bone fastener, as described herein. Drive interface 52 has a hex drive and/or bit configuration. In some embodiments, interface 52 and/or the surface of the bone fastener can include variously configured drive and/or socket surfaces, such as, for example, those described herein.

Figure 4:
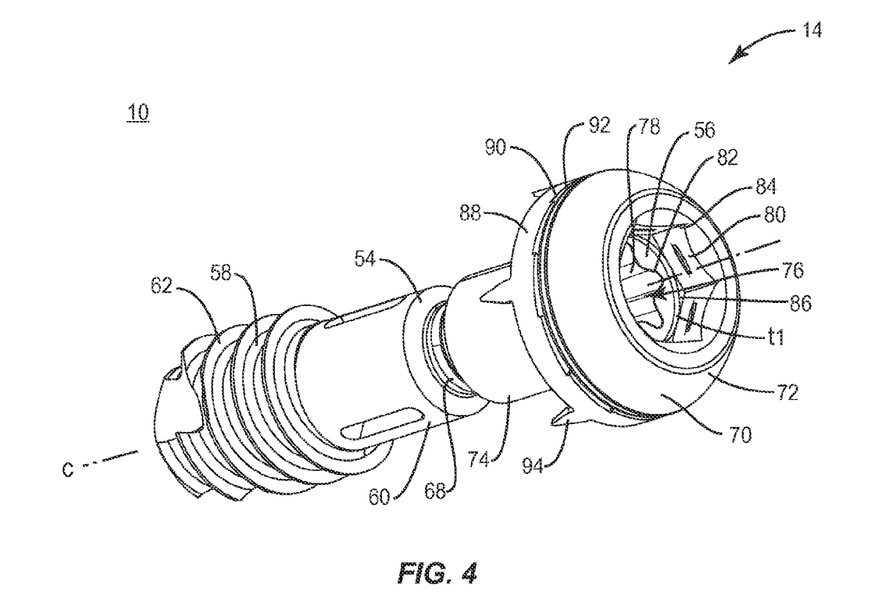
FIG. 4 is a perspective view of a component of one embodiment of a surgical implant system in accordance with the principles of the present disclosure.
Figure 5:
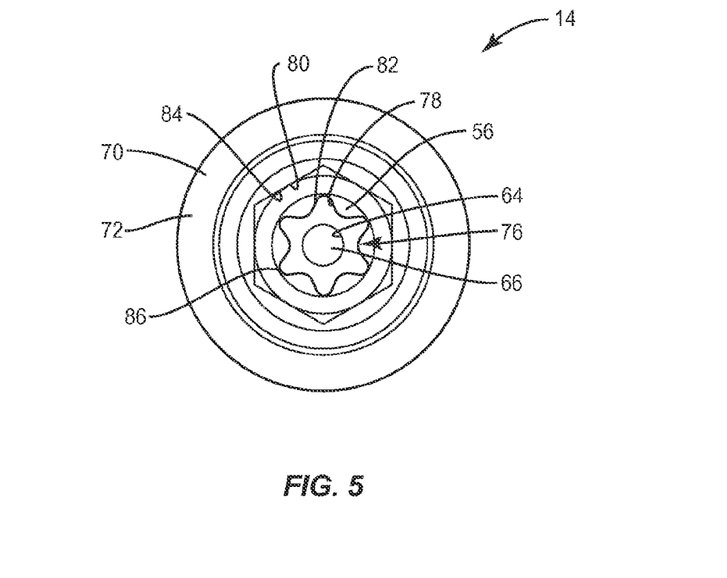
FIG. 5 is an end view of the component shown in FIG. 4.

Bone fastener 14, as shown in FIGS. 4 and 5, includes an inner member, such as, for example, shaft 54. Shaft 54 defines a longitudinal axis c that extends between an end 56 and an end 58. End 58 is configured for penetrating a sacrum, as described herein. In some embodiments, shaft 54 may have a solid, hollow, porous or cage configuration, and/or the overall and/or cross-sectional geometry of shaft 54 may be, for example, round, oval, oblong, triangular, rectangular, polygonal, irregular, uniform, non-uniform, consistent or variable.

Figure 6:
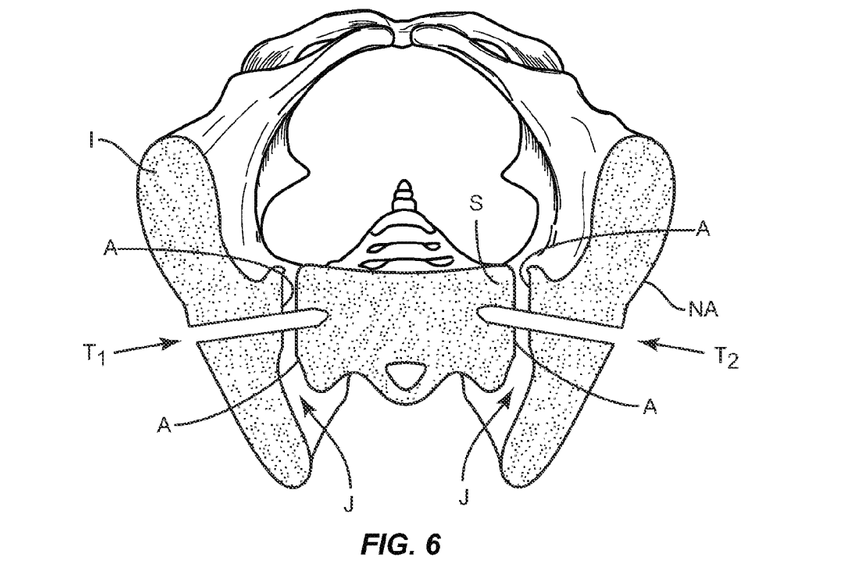
FIG. 6 is a perspective view of a sacro-iliac region.
Figure 7:
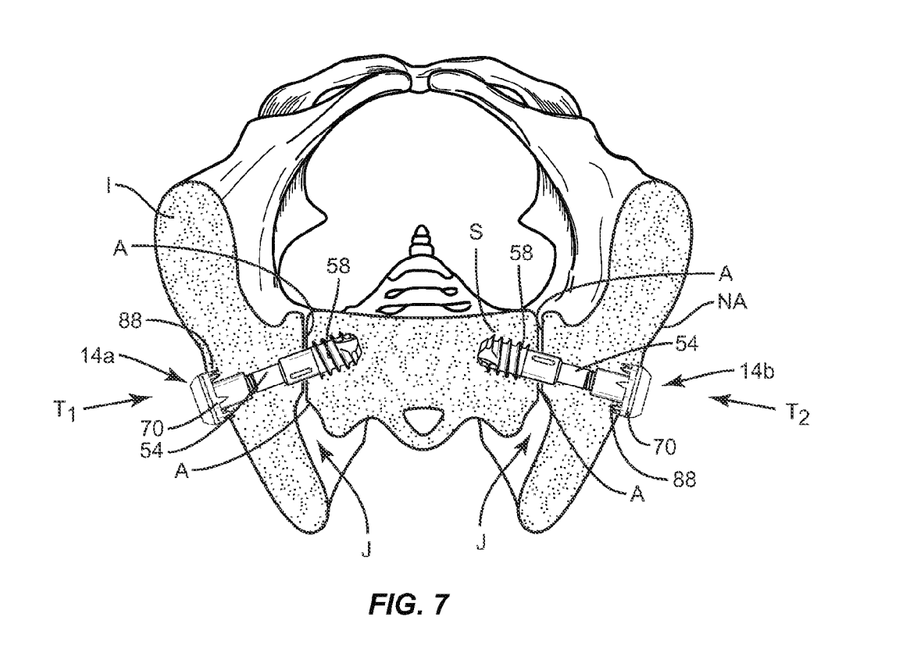
FIG. 7 is a perspective view of components of one embodiment of a surgical implant system in accordance with the principles of the present disclosure disposed with the sacro-iliac region.

Shaft 54 includes an outer surface 60 having a threaded portion 62 configured for threaded fixation with sacrum S of sacro-iliac joint J (FIGS. 6 and 7). Portion 62 is transarticular and penetrates tissues, including bone, of sacrum S to secure bone fastener 14 with sacro-iliac joint J for stabilization and immobilization thereof. In some embodiments, all or only a portion of portion 62 may be disposed with sacrum S, and that a portion of portion 62 may be disposed with ilium I of sacro-iliac joint J. In some embodiments, all or only a portion of portion 62 may have alternate surface configurations, for alternative fixation configurations with a body cavity, such as, for example, threaded, non-threaded, arcuate, undulating, substantially smooth, rough, spiked, semi-porous, dimpled and/or polished, textured for friction fit and/or oversized for pressure fit to facilitate fixation with tissues, including bone, of sacrum S, and/or include fastening elements such as anchors, barbs, spikes, detents and/or slots. In one embodiment, shaft 54 is cannulated and includes an inner surface 64 that defines a passageway 66 configured to disperse flowable materials, such as, for example, biologics, agents, medical adhesives, bonding cements and/or bone healing substances, as described herein.

Surface 60 includes a threaded portion 68 configured for threaded engagement during axial translation with a screw 70 of bone fastener 14. Screw 70 is configured for rotational threaded engagement with shaft 54 to cause axial translation of screw 70 relative to shaft 54 such that separated articular surfaces of the sacrum and the ilium are drawn into fixation and is configured for disposal within a body cavity formed in SI joint J. In one embodiment, screw 70 is rotatable independent of and relative to shaft 54.

Screw 70 includes a head 72 and a shaft 74. A surface of head 72 is serrated and configured for engagement with a fixation element, as described herein. Head 72 defines a tool socket 76 configured for engagement with a surgical instrument, such as, for example, driver 16 and/or driver 38, described herein, which attaches to bone fastener 14 so that bone fastener 14 can be driven into an implant space prepared by a medical device.

Socket 76 includes an inner surface defining a surface 78 and a surface 80 disposed in a serial configuration along axis c, with surface 78 being distal to surface 80. Surface 78 defines a socket interface 82 engageable with drive interface 32, described herein. Socket interface 82 has a hexalobular socket configuration. Surface 80 defines a socket interface 84 engageable with drive interface 34 and/or drive interface 52, described herein. Drive interface 84 has a hex socket configuration.

Interfaces 82, 84 are separated by a transition line t1 extending transverse to axis c. Interface 82 has a first diameter and interface 84 has a second diameter that is greater than the first diameter. Socket 76 includes an edge 86 disposed between interfaces 82, 84 and adjacent transition line t1. Interfaces 82, 84 and edge 86 are disposed in an orientation such that socket 76 includes a stepped configuration adjacent end 56.

In one embodiment, a fixation element, such as, for example, a washer 88 is configured for disposal with screw 70 and to penetrate the outer surface of Ilium I. Washer 88 includes serrations 90 configured for mated engagement with a serrated surface 92 of head 72. In one embodiment, the engagement of the serrated surfaces prevents backout of the components of bone fastener 14. Washer 88 includes at least one penetration element, such as, for example, spikes 94 configured for penetrating the outer surface of Ilium I. In some embodiments, washer 88 and/or screw 70 may have alternate gripping configurations, such as, for example, hooks, anchors, barbs, detents, openings, arcuate, undulating, rough, serrations, semi-porous, dimpled and/or textured to facilitate fixation with tissues, including bone.

In one embodiment, washer 88 is threaded with screw 70 for axial translation of washer 88 and disposal along shaft 74 and into contacting engagement with head 72. Upon disposal of washer 88 with screw 70 such that the proximal outer surface of washer 88 is in a contacting engagement with head 72, washer 88 is freely rotatable relative to the surface of screw 70 to facilitate penetration of spikes 94 with the outer surface of Ilium I. Upon penetration of spikes 94 with ilium I, the serrated surfaces of washer 88 and screw 70 are drawn into a fixed engagement. In one embodiment, bone fastener 14 does not include a washer and the surface of head 72 directly engages the outer surface of ilium I.

In operation, driver 16 is manipulated to dispose portion 26 with socket 76 such that interface 32 engages interface 82, and interface 34 engages interface 84. Handle 18 is manipulated to rotate shaft 20 in a clockwise or counterclockwise direction. Driver 16 engages bone fastener 14 to rotate and axially translate end 58 into penetrating engagement with tissue, such as, for example, a sacrum. Interface 32 engages interface 82 to rotate shaft 54 such that threads 62 penetrate and fix bone fastener 14 with the sacrum. Interface 34 engages interface 84 to rotate screw 70 with shaft 54. Screw 70 is rotatable independent of and relative to washer 88.

Portion 26 is removed from socket 76 and driver 38 is manipulated to dispose surface 50 with socket 76 such that interface 52 engages interface 84. Handle 40 is manipulated to rotate shaft 42 in a clockwise or counterclockwise direction. Driver 38 engages bone fastener 14 to draw separated articular surfaces of the sacrum and the ilium into fixation. Interface 52 engages interface 84 to rotate screw 70 independent of shaft 54.

As screw 70 is relatively rotated about shaft 54, the threaded inner surface of shaft 74 and threads 68 cooperatively engage such that shaft 54 moves relative to screw 70 along longitudinal axis c to facilitate axial translation of shaft 54. With end 58 anchored in sacrum S, axial translation of screw 70 causes washer 88 to be drawn into fixation with outer non-articular surface NA of ilium I, as described. With end 58 anchored in sacrum S and washer 88 disposed in engagement with outer non-articular surface NA, further rotation of screw 70 relative to shaft 54 with driver 38, axially translates screw 70 relative to shaft 54 in a configuration to draw separated articular surfaces A of sacrum S and ilium I into fixation to immobilize SI joint J.

In assembly, operation and use, as shown in FIGS. 6 and 7, surgical implant system 10, similar to the systems and methods described herein, includes surgical instrument 12 and one or a plurality of bone fasteners 14, described herein, which are employed with a surgical procedure for treatment of SI joints J of a patient. Surgical implant system 10 may also be employed with other surgical procedures, which may include one or all of the steps described herein. In some embodiments, surgical implant system 10 is employed with a surgical arthrodesis procedure, such as, for example, fusion for treatment of an applicable condition or injury of an affected SI joint J. In some embodiments, surgical implant system 10 including surgical instrument 12 and one or a plurality of bone fasteners 14 may be employed during a surgical fusion procedure for treatment of a condition or injury, such as, degeneration or fracture.

In use, to treat the affected section of SI joints J, a medical practitioner obtains access to a surgical site including each SI joint J in any appropriate manner, such as through incision and retraction of tissues. In some embodiments, surgical implant system 10 may be used in any existing surgical method or technique including open surgery, mini-open surgery, minimally invasive surgery and percutaneous surgical implantation, whereby SI joint J is accessed through a mini-incision, or sleeve that provides a protected passageway to the area. Once access to the surgical site is obtained, the particular surgical procedure is performed for treating the SI joint disorder. Surgical implant system 10 is employed to augment the surgical treatment. The components of surgical implant system 10 can be delivered or implanted as pre-assembled devices or can be assembled in situ. The components of surgical implant system 10 may be completely or partially revised, removed or replaced in situ. In some embodiments, one or all of the components of surgical implant system 10 can be delivered to the surgical site via manual manipulation and/or a free hand technique.

Trajectories T1, T2, as shown in FIG. 6, are defined for insertion of the components of surgical implant system 10 within SI joint J. In some embodiments, trajectory T1 may be oriented perpendicular, parallel, angularly offset, offset, cruciate and/or staggered relative to trajectory T2. The components of surgical implant system 10 are inserted via the protected passageway along each of the defined trajectories T1, T2 into SI joint J. Separate body cavities of SI joint J are prepared along each of trajectories T1, T2 for disposal of bone fasteners 14. In some embodiments, a guide wire and/or a trocar-cannula assembly may be employed as an instrument for gaining access to the surgical site and/or defining the trajectories.

The protected passageway includes a dilator/delivery tube (not shown) configured to deliver bone fasteners 14 adjacent to the joint space of SI joints J. In some embodiments, the dilator/delivery tube may be configured as an in-situ guidable instrument, and may include an endoscope camera tip for viewing insertion trajectory. In some embodiments, the components of surgical implant system 10 may be delivered and/or manipulated with a surgical site via imaging guidance and/or surgical navigation. In some embodiments, the components of surgical implant system 10 may include a cavity configured to receive the instrument to facilitate delivery of bone fasteners 14 to SI joints J. In some embodiments, the components of surgical implant system 10 may include a connecting portion, opening and/or mechanism, such as, for example, threaded holes, snap-on connects, and quick-connect mechanisms for connection to a delivery instrument for implant disposal, detachable connection and release and removal from the surgical site.

The body cavities are tapped and/or drilled in the joint surfaces of SI joint J in an orientation and alignment with sacrum S and ilium I. In some embodiments, a guide instrument (not shown) may be used to facilitate formation of such cavities by providing an alignment device for a surgical drill and/or tap. A first bone fastener 14a is delivered via the guide instrument to SI joint J into alignment with the body cavity along trajectory T1, as shown in FIG. 7. A second bone fastener 14b is similarly delivered via the guide instrument to SI joint J into alignment with the body cavity along trajectory T2. For each bone fastener 14, threaded portion 62 is threaded with the joint surfaces of SI joint J such that shaft 54 is fixed with the tissues of sacrum S, as described above.

Driver 16 is disposed with the protected passageway for engagement with bone fasteners 14a, 14b adjacent the surgical site. Driver 16 is manipulated to dispose portion 26 with socket 76. Handle 18 is manipulated to rotate shaft 20 in a clockwise direction. Driver 16 engages bone fasteners 14a, 14b to rotate and axially translate end 58 into penetrating engagement with sacrum S, as described herein.

Portion 26 is removed from socket 76 and driver 38 is manipulated to dispose surface 50 with socket 76 such that interface 52 engages interface 84. Handle 40 is manipulated to rotate shaft 42 in a clockwise direction. Driver 38 engages bone fasteners 14a, 14b to draw separated articular surfaces of sacrum S and ilium I into fixation, as described herein. With end 58 anchored in sacrum S, axial translation of screw 70 causes washer 88 to be drawn into fixation with outer non-articular surface NA of ilium I, as described. With end 58 anchored in sacrum S and washer 88 disposed in engagement with outer non-articular surface NA, further rotation of screw 70 relative to shaft 54 with driver 38, axially translates screw 70 relative to shaft 54 in a configuration to draw separated articular surfaces A of sacrum S and ilium I into fixation to secure, stabilize and immobilize SI joint J, as shown in FIG. 7, for arthrodesis.

In one embodiment, surgical implant system 10 includes fastening elements, such as, for example, screws (not shown) configured for fixation with articular surfaces A external to bone fasteners 14. The screws are employed to secure joint surfaces and provide complementary stabilization and immobilization to SI joints J. In some embodiments, bone fastener 14 may include locking structure such as, for example, clips, hooks, adhesives and/or flanges. In some embodiments, in joint fusion applications, the components of surgical implant system 10 include voids, cavities and/or openings for including therapeutic polynucleotides or polypeptides and bone growth promoting material, such as those described herein, which can be coated, packed or otherwise disposed therein.

In one embodiment, surgical implant system 10 can include one or a plurality of bone fasteners such as those described herein and/or fixation elements, which may be engaged with tissue in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, surgical implant system 10 may comprise various instruments, such as, for example, inserters, extenders, reducers, spreaders, distractors, blades, retractors, clamps, forceps, elevators and drills, which may be alternately sized and dimensioned, and arranged as a kit, according to the requirements of a particular application.

In some embodiments, surgical implant system 10 includes an agent, which may be disposed, coated, packed or layered within, on or about the components and/or surfaces of surgical implant system 10. In some embodiments, the agent may include bone growth promoting material, such as, for example, bone graft to enhance fixation of the fixation elements with vertebrae V. The components of surgical implant system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of surgical implant system 10 are removed from the surgical site and the incision is closed.

Figures 8, 9:
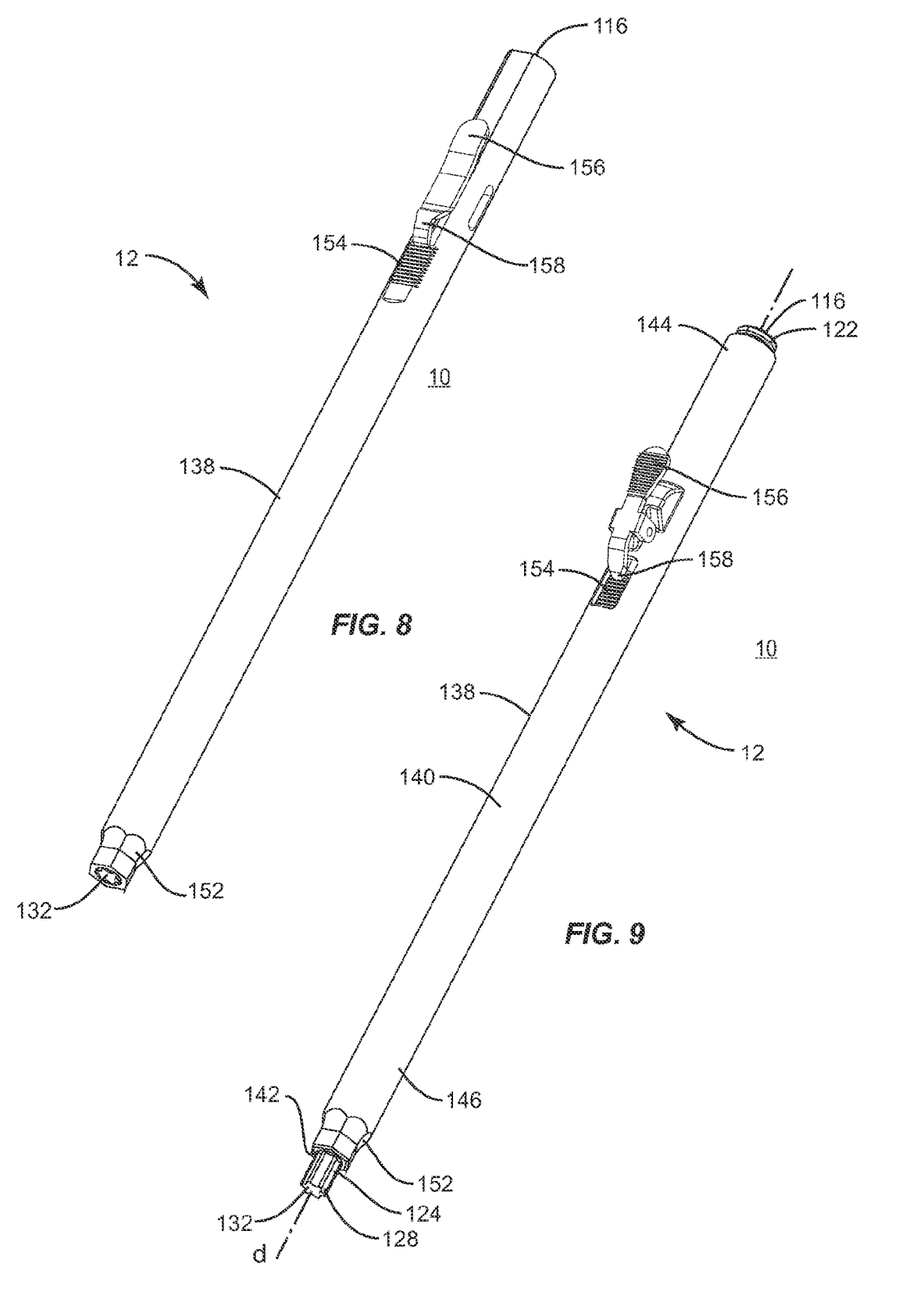
FIG. 8 is a perspective view of components of one embodiment of a surgical implant system in accordance with the principles of the present disclosure.
FIG. 9 is a perspective view of the components shown in FIG. 8.

In one embodiment, as shown in FIGS. 8 and 9, surgical implant system 10, similar to the systems and methods described above with regard to FIGS. 1-7, comprises surgical instrument 12, described herein, which includes a member, such as, for example, an inner shaft 116. Shaft 116 is elongated and extends in a linear configuration. In some embodiments, shaft 116 may extend in alternate orientations, such as, for example, arcuate, undulating, staggered, offset, angular and/or include one or a plurality of shaft members.

Shaft 116 extends between a first end, such as, for example, a proximal end 122 and a second end, such as, for example, a distal end 124. Shaft 116 has a cylindrical cross sectional configuration. In some embodiments, all or only a portion of shaft 116 may have alternate cross section configurations, such as, for example, oval, oblong, triangular, square, polygonal, irregular, uniform, non-uniform, offset, staggered, tubular and/or tapered. Shaft 116 defines a longitudinal axis d.

Distal end 124 includes an outer surface 128. Surface 128 defines a drive interface 132 engageable with interface 82, as described herein. Drive interface 132 has a hexalobular drive and/or bit configuration. In some embodiments, interface 132 can include variously configured drive surfaces, such as, for example, those described herein.

Surgical instrument 12 includes a member, such as, for example, an outer sleeve 138. Sleeve 138 includes a wall 140 that defines a tubular cavity 142 configured for disposal of shaft 116. Shaft 116 is coaxially disposed with sleeve 138 such that shaft 116 is axially translatable relative to sleeve 138 along cavity 142, as described below. In one embodiment, shaft 116 is disposed in a nested, concentric configuration with sleeve 138.

Sleeve 138 extends between a first end, such as, for example, a proximal end 144 and a second end, such as, for example, a distal end 146. Distal end 146 includes an outer surface defining a drive interface 152 engageable with interface 84, as described herein. Drive interface 152 has a hex drive and/or bit configuration. In some embodiments, interface 152 can include variously configured drive surfaces, such as, for example, those described herein.

Shaft 116 includes a locking surface, such as, for example, a toothed rack 154. Sleeve 138 includes a locking surface, such as, for example, a pivotable lever 156 having a pawl 158 for engagement with rack 154. Pawl 158 is selectively engageable with rack 154 to selectively fix orientation of shaft 116 relative to sleeve 138. Shaft 116 is axially translatable relative to sleeve 138 between a first orientation, as shown in FIG. 8, such that shaft 116 is retracted into sleeve 138 and interface 152 is engageable with interface 84, and a second orientation, as shown in FIG. 9, such that interface 132 extends distally from interface 152. In the second orientation, interface 132 is engageable with interface 82 and interface 152 is engageable with interface 84. In some embodiments, pawl 158 is resiliently biased into engagement with rack 154.

In operation, a gripping surface of lever 156 is engaged to rotate lever 156 relative to sleeve 138 and disengage pawl 158 from rack 154. Shaft 116 is axially translated relative to sleeve 138 to the second orientation, as described above. Lever 156 is released such that pawl 158 releasably engages rack 154 to selectively fix shaft 116 and sleeve 138 in the second orientation.

Instrument 12 is manipulated such that interface 132 engages interface 82, and interface 152 engages interface 84. Instrument 12 engages bone fastener 14 (FIGS. 4 and 5) to rotate and axially translate end 58 into penetrating engagement with tissue, such as, for example, a sacrum, as described.

The gripping surface of lever 156 is engaged to rotate lever 156 relative to sleeve 138 and disengage pawl 158 from rack 154. Shaft 116 is axially translated relative to sleeve 138 to the first orientation such that interface 132 is retracted into sleeve 138, as described above. Lever 156 is released such that pawl 158 releasably engages rack 154 to selectively fix shaft 116 and sleeve 138 in the first orientation. Interface 152 maintains engagement with interface 84 for rotating screw 70. Instrument 12 engages bone fastener 14 to draw separated articular surfaces of the sacrum and the ilium into fixation, as described. In some embodiments, in the first orientation, shaft 116 is disposed in a nested, concentric configuration with sleeve 138.

Figure 10:
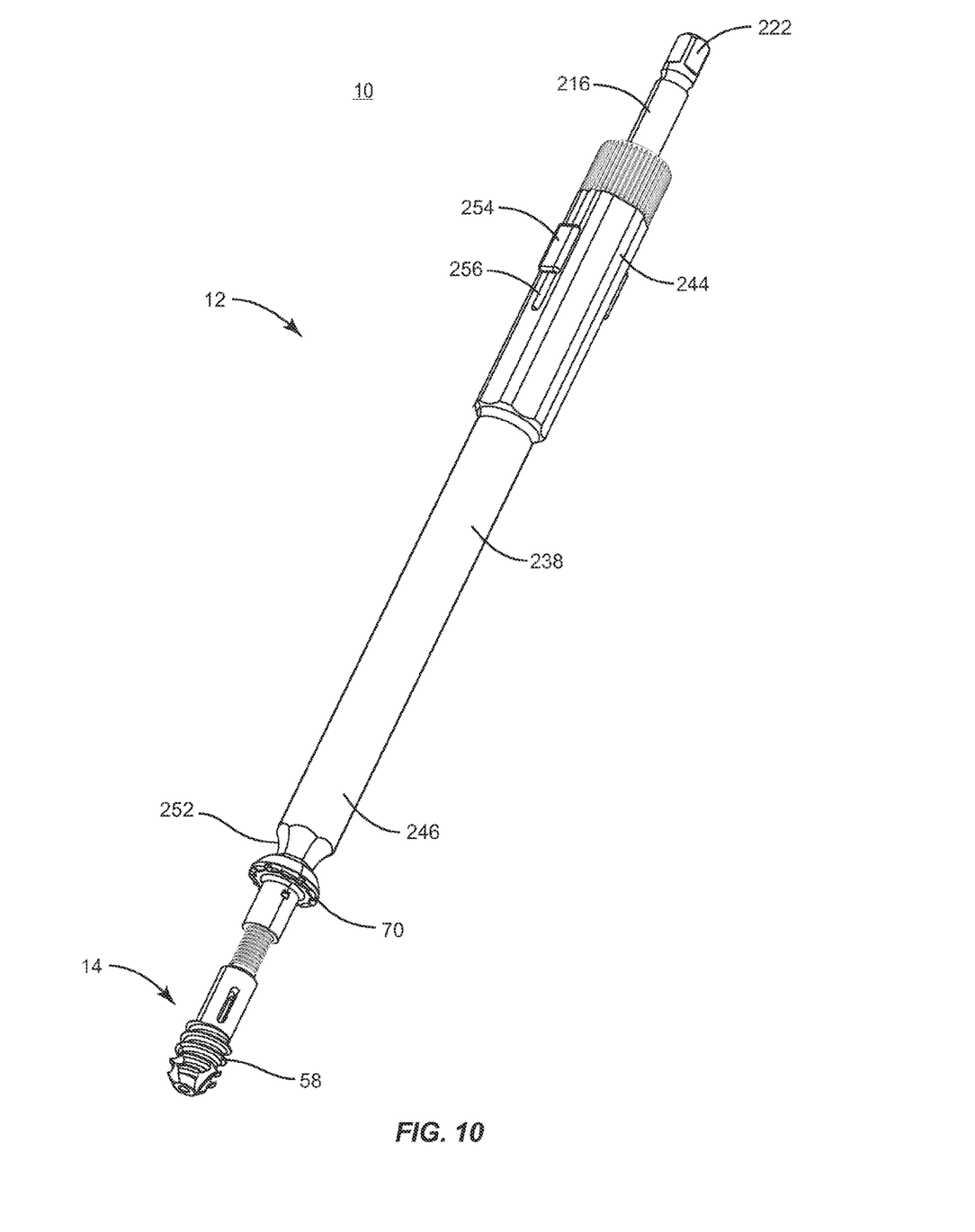
FIG. 10 is a perspective view of components of one embodiment of a surgical implant system in accordance with the principles of the present disclosure.

In one embodiment, as shown in FIG. 10, surgical implant system 10, similar to the systems and methods described above with regard to FIGS. 1-9, comprises surgical instrument 12, described herein, which includes an inner shaft 216, similar to shaft 116 described above. Shaft 216 extends between a proximal end 222 and a distal end (not shown) that includes a drive interface engageable with interface 82, as described herein. In some embodiments, end 222 is connected to a surgical tool and/or motorized driver, such as a drill, for rotation thereof.

An outer sleeve 238, similar to sleeve 138 described above, is configured for disposal of shaft 216 such that shaft 216 is coaxially disposed with sleeve 238. Shaft 216 is axially translatable relative to sleeve 238, as described below. Sleeve 238 extends between a proximal end 244 and a distal end 246. Distal end 246 includes an outer surface defining a drive interface 252 engageable with interface 84, as described herein.

Shaft 216 includes a slider 254. Sleeve 238 defines a slot 256 that defines movable limits of slider 254. Slider 254 is selectively movable along slot 256 to axially translate shaft 216 relative to sleeve 238 between a first orientation, similar to that described with regard to FIG. 8, and a second orientation, similar to that described with regard to FIG. 9. In the first orientation, slider 254 is disposed adjacent a proximal most end of slot 256 and shaft 216 is refracted into sleeve 238 such that interface 252 is engageable with interface 84. In the second orientation, slider 254 is disposed adjacent a distal most end of slot 256 and an interface, similar to interface 132, extends distally from interface 252 and the interface is engageable with interface 82 and interface 252 is engageable with interface 84.

In operation, a gripping surface of slider 254 is engaged to translate shaft 216 relative to sleeve 238 to the second orientation, as described above. Instrument 12 is manipulated such that the interface, similar to interface 132, engages interface 82, and interface 252 engages interface 84. Instrument 12 engages bone fastener 14 to rotate and axially translate end 58 into penetrating engagement with tissue, such as, for example, a sacrum, as described.

The gripping surface of slider 254 is engaged to translate shaft 216 relative to sleeve 238 to the first orientation such that the interface, similar to interface 132, is retracted into sleeve 238, as described above. Interface 252 maintains engagement with interface 84 for rotating screw 70. Instrument 12 engages bone fastener 14 to draw separated articular surfaces of the sacrum and the ilium into fixation, as described.

Figure 11:
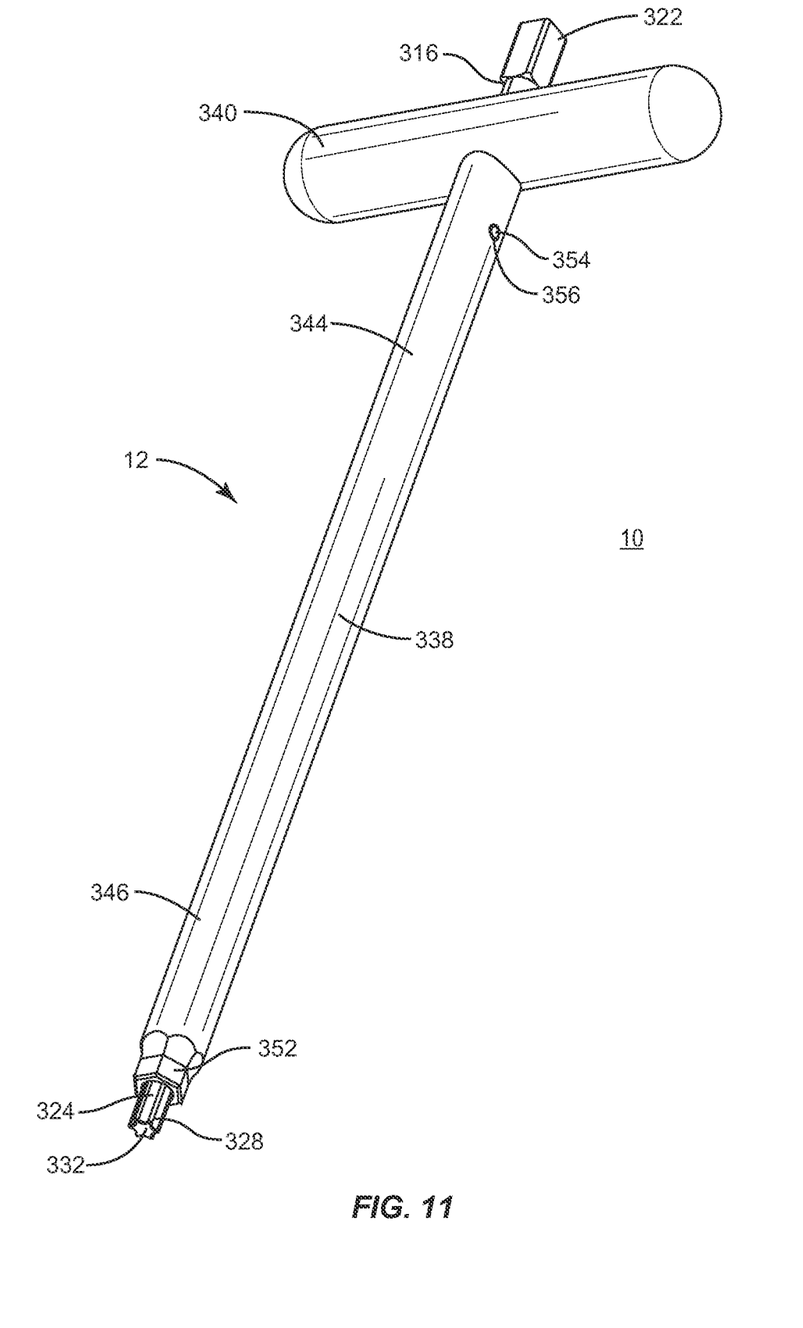
FIG. 11 is a perspective view of components of one embodiment of a surgical implant system in accordance with the principles of the present disclosure.

In one embodiment, as shown in FIG. 11, surgical implant system 10, similar to the systems and methods described above with regard to FIGS. 1-10, comprises surgical instrument 12, described herein, which includes an inner shaft 316, similar to shaft 216 described above. Shaft 316 extends between a proximal end 322 and a distal end 324. In some embodiments, end 322 is connected to a surgical tool and/or motorized driver, such as a drill, for rotation thereof.

Distal end 324 includes an outer surface 328. Surface 328 defines a drive interface 332 engageable with interface 82, as described herein. Drive interface 332 has a hexalobular drive and/or bit configuration. In some embodiments, interface 332 can include variously configured drive surfaces, such as, for example, those described herein.

An outer sleeve 338, similar to the sleeves described herein, includes a T-handle 340 and defines a tubular cavity configured for disposal of shaft 316. Shaft 316 is coaxially disposed with sleeve 338 such that shaft 316 is axially translatable relative to sleeve 338 along the cavity, as described below.

Sleeve 138 extends between a proximal end 344 and a distal end 346. Distal end 346 includes an outer surface defining a drive interface 352 engageable with interface 84, as described herein. Drive interface 352 has a hex drive and/or bit configuration. In some embodiments, interface 352 can include variously configured drive surfaces, such as, for example, those described herein.

Shaft 316 includes a locking surface, such as, for example, a retractable pin 354. Sleeve 338 includes a locking surface, such as, for example, surfaces that define an aperture 356. In operation, shaft 316 is disposed with sleeve 338 such that interface 332 extends distally from interface 352. Pin 354 is disposed with aperture 356 in an interference engagement to releasably fix shaft 316 with sleeve 338. Handle 340 is manipulated such that interface 332 engages interface 82, and interface 352 engages interface 84. Instrument 12 engages bone fastener 14 (FIGS. 4 and 5) to rotate and axially translate end 58 into penetrating engagement with tissue, such as, for example, a sacrum, as described.

Shaft 316 is translated proximally, relative to sleeve 338, for removal from sleeve 338 such that the interference of pin 354 with the surfaces of aperture 356 is overcome and shaft 316 is releasable from sleeve 338. Interface 352 maintains engagement with interface 84 for rotating screw 70. Instrument 12 engages bone fastener 14 to draw separated articular surfaces of the sacrum and the ilium into fixation, as described.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
   a bone fastener comprising a shaft having a threaded outer surface, a head having a threaded inner surface that engages the threaded outer surface, and a washer positioned between the head and the shaft;
   a first member defining a longitudinal axis and including a first drive interface engageable with a drive interface of the head and a second drive interface engageable with a drive interface of the shaft; and
   a second member including a drive interface engageable with the drive interface of the head,
   wherein the head is rotatable relative to the shaft to translate the head axially relative to the shaft and the washer is movable between a first configuration in which the washer is rotatable relative to the head and a second configuration in which the washer is fixed relative to the head.

2. A surgical system as recited in claim 1, wherein the first member comprises an anchor driver including an elongated shaft extending to the first drive interface and a T-shaped handle.

3. A surgical system as recited in claim 1, wherein the first drive interface and the second drive interface are disposed in a serial configuration along the longitudinal axis.

4. A surgical system as recited in claim 3, wherein the serial configuration includes a stepped orientation of the first and second drive interfaces.

5. A surgical system as recited in claim 1, wherein the second member comprises a compression driver including an elongated shaft extending to the drive interface of the second member and a T-shaped handle.

6. A surgical system as recited in claim 1, wherein the first member is separate from the second member.

7. A surgical system as recited in claim 1, wherein the second member is spaced apart from the drive interface of the shaft when the drive interface of the second member engages the drive interface of the head.

8. A surgical system as recited in claim 1, wherein the second drive interface is distal to the first drive interface along the longitudinal axis.

9. A surgical system as recited in claim 1, wherein the washer is rotatable relative to the shaft when the washer is in the first configuration.

10. A surgical system as recited in claim 1, wherein serrations of the washer engage a serrated surface of the head when the washer is in the second configuration.

11. A surgical system as recited in claim 1, wherein the bone fastener defines a second longitudinal axis and the washer includes at least one penetrating element that extends parallel to the second longitudinal axis.

12. A surgical system as recited in claim 1, wherein the bone fastener defines a second longitudinal axis and the washer includes a plurality of spikes disposed circumferentially about the washer that each extend parallel to the second longitudinal axis.

13. A surgical system as recited in claim 1, wherein the shaft and the head each include a flange and the head is configured to translate axially relative to the shaft in a first direction to engage the flanges with one another to prevent further translation of the head relative to the shaft in the first direction.

14. A surgical system as recited in claim 1, wherein the drive interface of the head comprises a socket having hex socket configuration and the drive interface of the shaft comprises a socket having a hexalobular socket configuration.

15. A surgical implant system comprising:
a first member defining a longitudinal axis and including a first drive interface and a second drive interface;
a second member that is separate from the first member and includes a drive interface; and
a bone fastener comprising an inner member configured for penetrating a sacrum, an outer member configured to engage an outer non-articular surface of an ilium, and a washer positioned between the inner and outer members,
wherein the second drive interface is engageable with the inner member and the first drive interface is engageable with the outer member to rotate the inner and outer members for fixation of the inner member with the sacrum,
wherein the drive interface of the second member is engageable with the outer member to rotate the outer member relative to the inner member to cause axial translation of the inner member relative to the outer member in a configuration such that separated articular surfaces of the sacrum and the ilium are drawn into fixation, and
wherein the washer is movable between a first configuration in which the washer is rotatable relative to the outer member and a second configuration in which the washer is fixed relative to the outer member.

16. A surgical implant system as recited in claim 15, wherein the first member comprises an anchor driver including an elongated shaft extending to the first drive interface and a T-shaped handle and the second member comprises a compression driver including an elongated shaft extending to the drive interface of the second member and a T-shaped handle.

17. A surgical implant system as recited in claim 15, wherein the outer member includes at least one fixation element oriented to penetrate an outer surface of the ilium.

18. A surgical implant system as recited in claim 15, wherein the first drive interface engages a socket of the outer member having a hex socket configuration and the second drive interface engages a socket of the inner member having a hexalobe socket configuration.

19. A surgical implant system as recited in claim 15, wherein:
serrations of the washer engage a serrated surface of the head when the washer is in the second configuration; and
the bone fastener defines a second longitudinal axis and the washer includes a plurality of spikes disposed circumferentially about the washer that each extend parallel to the second longitudinal axis.

20. A surgical system comprising:
a bone fastener comprising a shaft having a threaded outer surface, a head having a threaded inner surface that engages the threaded outer surface, and a washer that is positioned between the head and the shaft;
a first member defining a longitudinal axis and including a first drive interface engageable with a drive interface of the head having a hex socket configuration and a second drive interface engageable with a drive interface of the shaft having a hexalobe socket configuration; and
a second member including a drive interface engageable with the drive interface of the head,
wherein the head is rotatable relative to the shaft to translate the head axially relative to the shaft and the washer is movable between a first configuration in which the washer is rotatable relative to the head and a second configuration in which the washer is fixed relative to the head,
wherein serrations of the washer engage a serrated surface of the head when the washer is in the second configuration, and
wherein the bone fastener defines a second longitudinal axis and the washer includes a plurality of spikes disposed circumferentially about the washer that each extend parallel to the second longitudinal axis.

* * * * *

UNITED STATES PATENT AND TRADEMARK OFFICE
CERTIFICATE OF CORRECTION

PATENT NO. : 9,724,149 B2  
APPLICATION NO. : 13/789180  
DATED : August 8, 2017  
INVENTOR(S) : Trieu et al.

Page 1 of 1

It is certified that error appears in the above-identified patent and that said Letters Patent is hereby corrected as shown below:

On the Title Page

In Item (72), under "Inventors", in Column 1, Line 4, delete "Michael Simmons," and insert -- Michael C. Simmons," --, therefor.

In Item (73), under "Assignee", in Column 1, Line 1, delete "Orhtopedic," and insert -- Orthopedic, --, therefor.

In Item (57), under "ABSTRACT", in Column 2, Lines 10-11, delete "disclosed. Systems and methods are disclosed." and insert -- disclosed. --, therefor.

In the Specification

In Column 1, Line 67, delete "sacro-iliac" and insert -- sacroiliac --, therefor.

In Column 2, Line 4, delete "sacro-iliac" and insert -- sacroiliac --, therefor.

In Column 3, Line 8, delete "steps of" and insert -- steps of: --, therefor.

In Column 3, Line 17, delete "bony" and insert -- bone --, therefor.

In Column 7, Line 41, delete "sacro-iliac" and insert -- sacroiliac --, therefor.

In Column 7, Line 43, delete "sacro-iliac" and insert -- sacroiliac --, therefor.

In Column 7, Line 47, delete "sacro-iliac" and insert -- sacroiliac --, therefor.

In Column 8, Lines 18-19, delete "socket interface 84" and insert -- socket interface 82 --, therefor.

In Column 13, Line 16, delete "refracted" and insert -- retracted --, therefor.

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*